(12) United States Patent
Gao

(10) Patent No.: US 10,138,038 B2
(45) Date of Patent: Nov. 27, 2018

(54) ANTIMICROBIAL DETECTABLE CABLE TIE

(71) Applicant: Thomas & Betts International, LLC, Wilmington, DE (US)

(72) Inventor: Yan Gao, Memphis, TN (US)

(73) Assignee: Thomas & Betts International, LLC, Wilmington, DE (US)

( * ) Notice: Subject to any disclaimer, the term of this patent is extended or adjusted under 35 U.S.C. 154(b) by 287 days.

(21) Appl. No.: 14/725,075

(22) Filed: May 29, 2015

(65) Prior Publication Data

US 2015/0353250 A1   Dec. 10, 2015

Related U.S. Application Data

(60) Provisional application No. 62/008,167, filed on Jun. 5, 2014.

(51) Int. Cl.

| C09D 5/16 | (2006.01) |
| B65D 63/10 | (2006.01) |
| B29D 5/08 | (2006.01) |
| A01N 59/26 | (2006.01) |
| A01N 25/34 | (2006.01) |
| B29K 77/00 | (2006.01) |
| B29K 23/00 | (2006.01) |

(52) U.S. Cl.
CPC ......... B65D 63/1027 (2013.01); A01N 25/34 (2013.01); A01N 59/26 (2013.01); B29D 5/08 (2013.01); B65D 63/1036 (2013.01); B29K 2023/12 (2013.01); B29K 2077/00 (2013.01); B29K 2995/0037 (2013.01); B65D 2563/101 (2013.01); Y10T 24/1498 (2015.01)

(58) Field of Classification Search
None
See application file for complete search history.

(56) References Cited

U.S. PATENT DOCUMENTS

| 5,102,075 A | 4/1992 | Dyer |
| 5,513,421 A | 5/1996 | Wells |
| 5,815,891 A * | 10/1998 | Students ............ B65D 63/1036 24/16 PB |
| 7,017,237 B2 | 3/2006 | Magno, Jr. et al. |
| 2004/0094243 A1* | 5/2004 | Wynne, III ............... C22C 9/04 148/433 |
| 2006/0110456 A1 | 5/2006 | Teo et al. |
| 2007/0226960 A1 | 10/2007 | LaPorte et al. |
| 2007/0234525 A1 | 10/2007 | LaPorte et al. |
| 2008/0044458 A1* | 2/2008 | MacDonald ........... A01N 59/16 424/443 |
| 2008/0102122 A1 | 5/2008 | Mahadevan et al. |
| 2009/0259251 A1 | 10/2009 | Cohen |
| 2012/0245629 A1 | 9/2012 | Gross et al. |
| 2015/0086597 A1 | 3/2015 | Mallak et al. |
| 2015/0353250 A1 | 12/2015 | Gao |

FOREIGN PATENT DOCUMENTS

| EP | 0919756 A2 | 6/1999 |
| EP | 1843070 A2 | 10/2007 |
| EP | 2952094 A1 | 12/2015 |
| JP | 08090674 A | 4/1996 |
| JP | 10292107 A | 11/1998 |
| JP | 2003-073531 A | 3/2003 |
| JP | 2009-520076 A | 5/2009 |
| JP | 2011-513532 A | 4/2011 |
| JP | 2011-178416 A | 9/2011 |
| JP | 2014-088952 A | 5/2014 |
| WO | 2005061022 A2 | 7/2005 |
| WO | 2006015317 A2 | 2/2006 |
| WO | 2006/036581 A2 | 4/2006 |
| WO | 2007/070650 A2 | 6/2007 |
| WO | 2008150460 A1 | 12/2008 |
| WO | 2009/108158 A1 | 9/2009 |
| WO | 2012027863 | 3/2012 |
| WO | 2013071474 A1 | 5/2013 |
| WO | 2013121169 A2 | 8/2013 |

OTHER PUBLICATIONS

Grass et al. Applied and Environmental Microbiology, Mar. 2011, p. 1541-1547.*
Zhu et al. (Food Microbiology 30 (2012) 303-310).*
Wikipedia, 'Antimicrobial copper-alloy touch surfaces', Internet Archive Oct. 19, 2010, https://web.archive.org/web/20101019203213/https://en.wikipedia.org/wiki/Antimicrobial_copper-alloy_touch_surfaces.

* cited by examiner

Primary Examiner — Robert T Butcher
(74) Attorney, Agent, or Firm — Taft Stettinius & Hollister LLP

(57) ABSTRACT

Cable ties including an antimicrobial additive and a detectable component as well as methods of making the same. More particularly, cable ties including a composition having a base plastic, an antimicrobial additive and a detectable additive selected from a detectable metal additive, an X-ray detectable additive, and combinations thereof. Also, cable ties including a composition and an antimicrobial metallic barb material wherein the composition includes a base plastic and an antimicrobial additive.

15 Claims, 1 Drawing Sheet

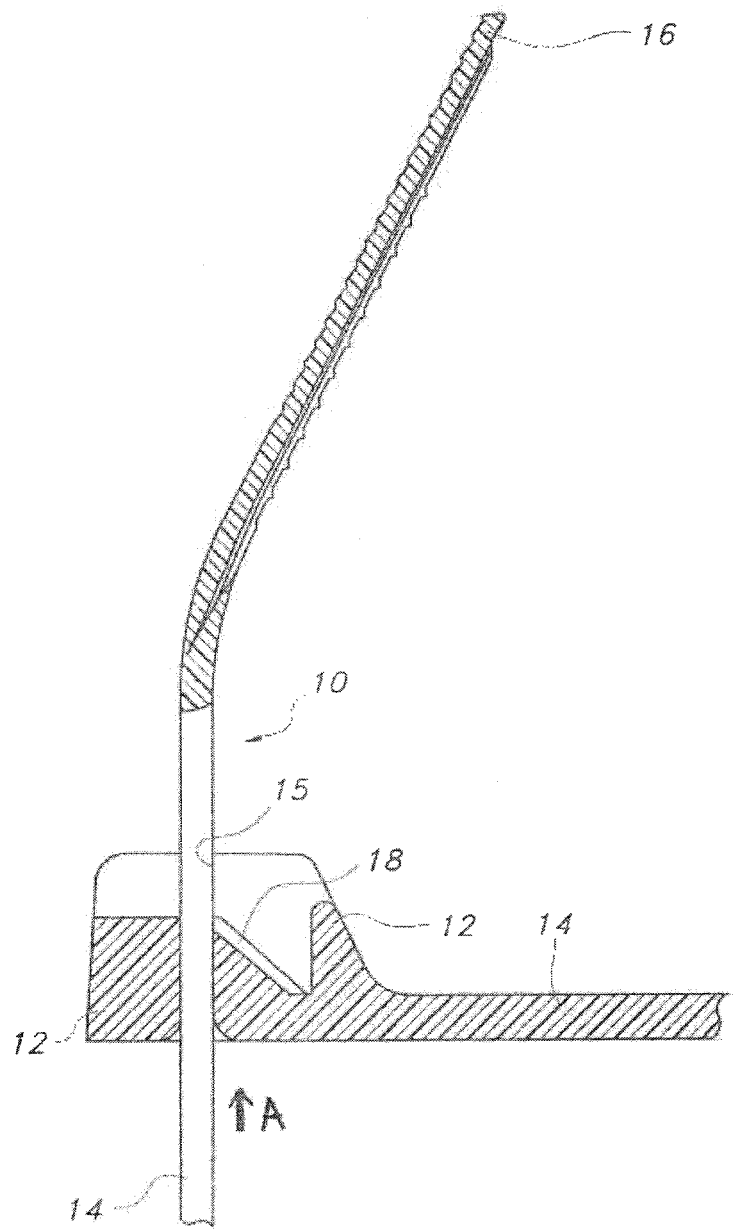

ANTIMICROBIAL DETECTABLE CABLE TIE

CROSS-REFERENCE TO RELATED APPLICATION

This application claims the benefit of U.S. Provisional Application No. 62/008,167, filed Jun. 5, 2014 the entire contents of which are incorporated by reference herein.

FIELD OF THE INVENTION

The present invention relates to cable ties having antimicrobial properties that are detectable as well as methods of making the same. More particularly, the present invention is directed to cable ties including a composition having a base plastic (e.g., polyamide or polypropylene), an antimicrobial additive and a detectable additive selected from a detectable metal additive, an X-ray detectable additive, and combinations thereof. Also, the present invention is directed to cable ties including a composition and an antimicrobial metallic barb material wherein the composition includes a base plastic and an antimicrobial additive.

BACKGROUND OF THE INVENTION

Cable ties are well known and may be used to bundle or secure a group of articles such as electrical wires or cables. Typically, cable ties include a head, elongate tail and a longitudinal strap therebetween. The head of the cable tie includes a locking element which is engageable with the strap to secure the strap in the head.

There are generally two types of cable ties. The first is a one-piece cable tie. The one-piece tie is integrally formed of plastic material, preferably polyamide, and uses a molded pawl inside the head and a formed teeth array in the strap body to secure the strap in the tail. The second is a two-piece cable tie. The two-piece tie has a polyamide head and strap body. A metallic (e.g., stainless steel) barb is embedded in the head which digs into the strap to secure the strap in the body.

Generally, existing polyamide 6,6 or polypropylene detectable cable ties provide metal detectability and/or X-ray detectability when the cable tie or a fraction thereof is mixed with non-metallic materials (e.g., food or food ingredient). Such cable ties, used for food and food ingredients, are oftentimes stored in a warm environment having generally high humidity (e.g., a food processing facility). As warm and humid conditions are conducive to bacterial growth, bacteria can grow on the surface of a cable tie and not only develop unfavorable stains and odor over time but also introduce bacterial contamination into a food or food ingredient before the affected cable tie is detected and separated from contact with a food or food ingredient. Likewise, a hospital environment, such as a surgery room, typically includes various medical equipment that use cable ties for harness purposes. Undesirably, different types of bacteria and/or fungi may be introduced to the surface of such cable ties by exposure, such as by direct contact and/or via air, from an infected individual and transmitted to other individuals (e.g., a patient or caregiver). Thus, there is a need for cable ties that exhibit antimicrobial properties.

SUMMARY OF THE INVENTION

The present invention provides cable ties having antimicrobial properties that provide X-ray detectability and/or metal detectability. In particular, the cable ties include a composition having a base plastic, an antimicrobial additive, and a detectable additive selected from a detectable metal additive, an X-ray detectable additive and combinations thereof.

The present invention further provides cable ties including a composition wherein the composition includes a base plastic and an antimicrobial additive and the cable tie further includes an antimicrobial metallic barb material.

The present invention also provides methods of preparing cable ties including the steps of: mixing ingredients including a base plastic, an antimicrobial additive, and a detectable additive selected from a detectable metal additive, an X-ray detectable additive and combinations thereof to form a mixture; melting the mixture at a temperature that is between 1 and 30° C. above the melting point of the base plastic to form a molten material therefrom; and molding the cable tie from the molten material.

Advantageously, in addition to metal and/or X-ray detectability such cable ties provide protection from surface stain and odor caused by microbes (e.g., bacteria and/or fungi). Further, such cable ties reduce the possibility of microbial (e.g., bacterial and/or fungal) contamination, for example, in a food processing environment, when the cable tie is contacted with a food or food ingredient, or in a hospital environment, when the cable tie is exposed to a patient.

BRIEF DESCRIPTION OF THE FIGURE

FIG. 1 shows, in section, an exemplary cable tie of the present invention, having a cable tie head and extending strap, with the strap inserted into the head.

DETAILED DESCRIPTION OF THE INVENTION

Referring to FIG. 1, a cable tie 10 of the present invention is shown. Cable tie 10 is typically an elongate molded plastic member which is used in a manner well known in the art to wrap around a bundle of articles (not shown). Cable tie 10, including a composition that includes a base plastic, an antimicrobial additive, and a detectable additive selected from a detectable metal additive, an X-ray detectable additive and combinations thereof, which in certain embodiments, is suitable for use with food and food grade materials. Cable tie 10 has a head 12 at one end thereof, a tail 16 at the other end of the head 12 and a generally planar strap 14 therebetween. In the illustrative embodiment provided, head 12 is formed as an integral portion of cable tie 10. However, in certain applications cable tie 10 may be constructed in a manner where head 12 is formed separately from strap 14.

Head 12 of cable tie 10 includes an aperture 15 therethrough (shown with strap 14 therein) for insertably accommodating the tail 16 and passage of the strap 14 therein in a first direction "A". Head 12 of cable tie 10 includes a locking device 18 supported by the head 12 and extending into the aperture. The locking device permits movement of the strap 14 in the first direction "A" and prevents substantial movement of the strap 14 in a second direction "B" opposite the first direction upon an attempt to withdraw the strap 14 from the aperture. The locking device may include a metallic barb such as shown in U.S. Pat. No. 5,513,421; or an integrally formed plastic pawl such as shown in U.S. Pat. No. 7,017,237.

Suitable base plastics include, but are not limited to, polyamide (e.g., nylon), polypropylene, polycarbonate, poly(ethylene tetrafluoroethylene), polyetheretherketone, poly (ethylene and chlorotrifluoroethylene), polyvinyl chloride and combinations of two or more thereof. Base plastic is loaded at between 90 to 110 phr. In one embodiment, the base plastic is polypropylene. In one embodiment, the base plastic is polyamide. In one embodiment, the base plastic is polyamide 6 (i.e., nylon 6). In one embodiment, the base plastic is polyamide 6,6 (i.e., nylon 6,6). In one embodiment, base plastic is polyamide 6,6 loaded at 100 phr. In one embodiment, polyamide 6,6 loaded at 100 phr is a medium impact modified compound with embedded process aid.

Suitable antimicrobial additives include, but are not limited to, silver ion complex, copper ion complex, polychloro phenoxy phenol derivative, quaternary ammonium compound, zinc pyrithione derivative and combinations of two or more thereof. In one embodiment, the antimicrobial additive is loaded at between 0.5 phr to 2 phr. In one embodiment, the antimicrobial additive is silver sodium hydrogen zirconium phosphate. In one embodiment, the antimicrobial additive is silver sodium hydrogen zirconium phosphate loaded at between 0.5 phr to 2 phr. In one embodiment, the antimicrobial additive is silver sodium hydrogen zirconium phosphate loaded at 1 phr. As is well known to a skilled artisan, the amount of antimicrobial additive in the composition can be varied, depending on the antimicrobial additive selected and/or other ingredients employed, so as to provide antibacterial properties to the resultant cable tie.

Suitable detectable metal additives include, but are not limited to, ferrous metal particles, non-ferrous metal particles and combinations of two or more thereof. In one embodiment, the detectable metal additive is iron particles. Iron particles, other ferrous metal particles and/or non-ferrous particles can have various shapes (e.g., spherical shape, flake shape or other irregular shapes). The particle size of detectable metal additives can range from between 100 μm to 500 μm. Detectable metal additives are loaded at between 1 phr to 25 phr. In one embodiment, the detectable metal additive is iron particles having a particle size range of from 150 μm to 200 μm loaded at 21 phr. As is well known to a skilled artisan, the amount of detectable metal additive in the composition can be varied, depending on shape and size of particles thereof, to provide metal detectability to the resultant cable tie.

Suitable X-ray detectable additives include, but are not limited to, iodine, barium based salt and combinations of two or more thereof. In one embodiment, the X-ray detectable additive is barium sulfate. In one embodiment, X-ray detectable additive is loaded at between 4 phr to 8 phr. In one embodiment, the X-ray detectable additive is barium sulfate powder loaded at between 4 phr to 8 phr. In one embodiment, barium sulfate is loaded at 7 phr. As is well known to a skilled artisan, the amount of X-ray detectable additive in the composition can be varied, depending on other ingredients, to provide X-ray detectability to the resultant cable tie.

In one embodiment, the cable tie further comprises an antimicrobial metallic barb material.

Suitable antimicrobial metallic barb materials include, but are not limited to, copper alloy with an amount of copper between 62% and 99.99% therein (e.g., C11000, C51000, C70600, C26000, C75200, and C28000). In one embodiment, the antimicrobial metallic barb material includes C28000 copper.

In one embodiment, the composition further includes a colorant. A skilled artisan can readily select a colorant compatible with the composition. In one embodiment, the colorant is loaded at between 1 phr to 8 phr.

In one embodiment, the detectable additive includes a combination of a detectable metal additive and an X-ray detectable additive. In one such embodiment, the detectable metal additive is iron particles and the X-ray detectable additive is barium sulfate.

In one embodiment, the base plastic is polyamide 6,6, the antimicrobial additive is silver sodium hydrogen zirconium phosphate, the detectable additive includes a combination of a detectable metal additive and an X-ray detectable additive, wherein the detectable metal additive is iron particles and the X-ray detectable additive is barium sulfate. In one such embodiment, the base plastic is polyamide 6,6 loaded at 100 phr, the silver sodium hydrogen zirconium phosphate is loaded at 1 phr, the iron particles have a size range of 150 μm to 200 μm and are loaded at 21 phr, and the barium sulfate is loaded at 7 phr.

In one embodiment, any of the aforementioned cable ties of the present invention is treated with sanitizing chemical to inhibit antimicrobial (e.g., bacterial and/or fungal) growth. For example, sanitizing chemical can be applied once, daily, every other day or as deemed necessary to inhibit antimicrobial growth. In one embodiment, a cable tie of the present application is sanitized with 0.5% sodium hyperchlorite aqueous solution (widely used in hospital environments as a cleaning agent), for example, every other day. As is well known to a skilled artisan, sterilization procedures compatible for cleaning detectable plastic cable ties may be employed so as to minimize bacterial and/or fungal growth.

In general, methods of preparing cable ties are provided which include (a) mixing ingredients including a base plastic, an antimicrobial additive, and a detectable additive selected from a detectable metal additive, an X-ray detectable additive and combinations thereof; (b) melting the mixture at a temperature that is between 1 and 30° C. above the melting point of the base plastic to form a molten material therefrom and (c) molding the cable tie from the molten material. Technology that forms such composition is well known to a skilled artisan. Likewise, molding process technology for cable tie products is well known to a skilled artisan.

More specifically, the present invention provides methods of preparing a cable tie including mixing the ingredients (including a base plastic, an antimicrobial additive, and a detectable additive selected from a detectable metal additive, an X-ray detectable additive and combinations thereof) mechanically, followed by a heated melting process that undergoes further pressurized mechanical mixing to form a molten mixture wherein the temperature is controlled at between 1 and 30° C. above the melting point of the base plastic. The molten mixture is then pressed flowing into a steel mold, forming a cable tie shape. The plastic part is cooled down to yield a cable tie exhibiting both antimicrobial properties and metal and/or X-ray detectable properties.

In one embodiment, the base plastic is polyamide, polypropylene, polycarbonate, poly(ethylene tetrafluoroethylene), polyetheretherketone, poly(ethylene and chlorotrifluoroethylene), polyvinyl chloride, or a combination of two or more thereof. In one embodiment, the antimicrobial additive is selected from the group consisting of silver ion complex, copper ion complex, polychloro phenoxy phenol derivative, quaternary ammonium compound, zinc pyrithione derivative and combinations of two or more thereof. In one embodiment, the antimicrobial additive is loaded at between 0.5 phr to 2 phr. In one embodiment, the antimicrobial additive is silver sodium hydrogen zirconium phosphate. In one embodiment, the detectable additive includes a combination of a detectable metal additive and an X-ray detectable additive.

Though not meant to be limited by any theory with the subject invention, it is believed that incorporation of an antimicrobial additive in a composition (having at least one detectable additive therein) from which a cable tie is molded provides antimicrobial properties thereto. In particular, it is believed that such cable ties exhibit reduced surface stain and odor caused by bacteria and/or fungus. Further, it is believed that such cable ties reduce the possibility of microbial (e.g., bacterial and/or fungal) contamination when the cable ties are contacted with or exposed to a food, a food ingredient, or an individual.

As is well known to a skilled artisan, metal detectability of a cable tie can be tested using a metal detector. In one embodiment, a metal detecting device is able to detect a cable tie of the present invention at a setting of 0.170 cm/ferrous sphere.

As is well known to a skilled artisan, X-ray detectability of a cable tie can be tested using an X-ray detector. In one embodiment, an X-ray detecting device (e.g., Eagle FA detector from Smith-Heimann) is able to detect the presence of a cable tie of the present invention.

As is well known to a skilled artisan, antimicrobial properties of a cable tie of the present invention can be ascertained by measuring growth of a representative microbe thereon following incubation under conditions conducive to microbial growth as compared with a similarly treated conventional cable tie (i.e., lacking an antimicrobial additive). In one embodiment, a cable of the present invention is subjected to an antimicrobial test following either JIS Z2801 or iso22196 testing standard for representative bacteria. Desirably, a cable tie of the present invention will exhibit a >99.9% reduction of *Escherichia coli* and >99% reduction of *Staphylococcus aureus*. In another embodiment, a cable tie of the present invention exhibits the aforementioned antimicrobial activity and further exhibits favorable aging under accelerated aging conditions. For example, accelerated aging conditions for a polyamide 6,6-based antimicrobial cable tie are 60° C. and 50% relative humidity for 54 days, equating to two years of regular application at normal atmosphere.

It will be appreciated by those skilled in the art that changes could be made to the embodiments described above without departing from the broad inventive concept thereof. It is understood, therefore, that this invention is not limited to the particular embodiments disclosed, but is intended to cover modifications that are within the spirit and scope of the invention, as defined by the appended claims.

What is claimed is:

1. A cable tie comprising:
   a body having a composition wherein the composition comprises a base plastic, an antimicrobial additive, and a detectable additive selected from a detectable metal additive, an X-ray detectable additive and combinations thereof, and wherein the antimicrobial additive includes silver ion complex and at least one selected from the group consisting of copper ion complex, polychloro phenoxy phenol derivative, quaternary ammonium compound, and zinc pyrithione derivative, and
   a head having a barb comprising an antimicrobial metallic barb material,
   wherein the body and the head are integrally connected, and wherein the antimicrobial metallic barb material comprises a copper alloy selected from the group consisting of C28000, C11000, C51000, C70600, C26000, and C75200.

2. The cable tie of claim 1, wherein the base plastic is polyamide, polypropylene, polycarbonate, poly(ethylene tetrafluoroethylene), polyetheretherketone, poly(ethylene and chlorotrifluoroethylene), polyvinyl chloride, or a combination of two or more thereof.

3. The cable tie of claim 1, wherein the base plastic is polypropylene.

4. The cable tie of claim 1, wherein the base plastic is polyamide.

5. The cable tie of claim 1, wherein the base plastic is polyamide 6,6.

6. The cable tie of claim 1, wherein the antimicrobial additive is loaded at between 0.5 phr to 2 phr.

7. The cable tie of claim 1, wherein the silver ion complex is silver sodium hydrogen zirconium phosphate.

8. The cable tie of claim 1, wherein the detectable additive includes the detectable metal additive loaded at between 1 phr to 25 phr.

9. The cable tie of claim 1, wherein the detectable additive includes the X-ray detectable additive loaded at between 4 phr to 8 phr.

10. The cable tie of claim 1, wherein the composition further comprises a colorant.

11. A cable tie comprising a composition and an antimicrobial metallic barb material wherein the composition comprises a base plastic and an antimicrobial additive, wherein the antimicrobial additive includes silver ion complex and at least one selected from the group consisting of copper ion complex, polychloro phenoxy phenol derivative, quaternary ammonium compound, and zinc pyrithione derivative, and wherein the antimicrobial metallic barb material comprises a copper alloy selected from the group consisting of C28000, C11000, C51000, C70600, C26000, and C75200.

12. A method of preparing the cable tie of claim 1, the method comprising the steps of:
   mixing ingredients comprising the base plastic, the antimicrobial additive, and the detectable additive selected from the detectable metal additive, the X-ray detectable additive and combinations thereof to form a mixture;
   melting the mixture at a temperature that is between 1 and 30° C. above the melting point of the base plastic to form a molten material therefrom; and
   molding the cable tie from the molten material.

13. The method of claim 12, wherein the base plastic is polyamide, polypropylene, polycarbonate, poly(ethylene tetrafluoroethylene), polyetheretherketone, poly(ethylene and chlorotrifluoroethylene), polyvinyl chloride, or a combination of two or more thereof.

14. The method of claim 12, wherein the antimicrobial additive is loaded at between 0.5 phr to 2 phr.

15. The method of claim 12, wherein the silver ion complex is silver sodium hydrogen zirconium phosphate.

* * * * *